(12) United States Patent
Chen et al.

(10) Patent No.: US 11,425,905 B2
(45) Date of Patent: Aug. 30, 2022

(54) ANTIMICROBIAL PREVENTIVE NETTING

(71) Applicants: University of Washington, Seattle, WA (US); Seattle Children's Hospital, Seattle, WA (US)

(72) Inventors: James Chen, Seattle, WA (US); Tanner Clark, Seattle, WA (US); Thomas Lendvay, Seattle, WA (US)

(73) Assignees: University of Washington, Seattle, WA (US); Seattle Children's Hospital, Seattle, WA (US)

( * ) Notice: Subject to any disclaimer, the term of this patent is extended or adjusted under 35 U.S.C. 154(b) by 0 days.

(21) Appl. No.: 17/244,688

(22) Filed: Apr. 29, 2021

(65) Prior Publication Data

US 2022/0061318 A1 Mar. 3, 2022

Related U.S. Application Data

(60) Provisional application No. 63/073,652, filed on Sep. 2, 2020.

(51) Int. Cl.
*A01N 25/34* (2006.01)
*A41D 31/30* (2019.01)
(Continued)

(52) U.S. Cl.
CPC ............ *A01N 25/34* (2013.01); *A01N 43/16* (2013.01); *A01N 43/84* (2013.01); *A01N 43/90* (2013.01); *A41D 31/305* (2019.02); *A61L 9/18* (2013.01); *A62B 18/02* (2013.01); *A62B 31/00* (2013.01); *E04H 15/46* (2013.01); *E04H 15/54* (2013.01);
(Continued)

(58) Field of Classification Search
CPC ...... A01N 25/34; A41D 31/305; A41D 31/30; A61L 9/205
See application file for complete search history.

(56) References Cited

U.S. PATENT DOCUMENTS 3,817,389 A 6/1974 Weichselbaum
4,395,789 A 8/1983 Bruce
(Continued)

FOREIGN PATENT DOCUMENTS

CA 2276023 C 4/2002
CA 2473924 A1 7/2003
(Continued)

OTHER PUBLICATIONS

Midden, R.W., Wang, S.Y., "Singlet Oxygen Generation for Solution Kinetics: Clean and Simple," Journal of the American Chemical Society, 105(13):4129-4135, Jun. 29, 1983.
(Continued)

*Primary Examiner* — Kevin Joyner
(74) *Attorney, Agent, or Firm* — Christensen O'Connor Johnson Kindness PLLC

(57) ABSTRACT

An antimicrobial preventive netting is disclosed that includes one or more photosensitizers that are capable of generating a cloud of singlet oxygen on each surface and openings through the netting in response to incident light. A depth of the singlet oxygen cloud may be less than 0.7 centimeters from a netting surface. The netting may be supported by screens, enclosures or headgear. The netting can be made by dipping or soaking the netting in a solution of one or more photosensitizers.

15 Claims, 7 Drawing Sheets

(51) Int. Cl.
| | | |
|---|---|---|
| *A61L 9/20* | (2006.01) | |
| *A01N 43/84* | (2006.01) | |
| *A01N 43/16* | (2006.01) | |
| *A01N 43/90* | (2006.01) | |
| *A61L 9/18* | (2006.01) | |
| *E04H 15/54* | (2006.01) | |
| *A62B 18/02* | (2006.01) | |
| *A62B 31/00* | (2006.01) | |
| *E04H 15/46* | (2006.01) | |

(52) U.S. Cl.
CPC ....... *A61L 2209/12* (2013.01); *A61L 2209/14* (2013.01)

(56) References Cited

U.S. PATENT DOCUMENTS

| | | | |
|---|---|---|---|
| 4,402,318 | A | 9/1983 | Swartz |
| 5,445,608 | A | 8/1995 | Chen et al. |
| 5,715,837 | A | 2/1998 | Chen |
| 5,741,316 | A | 4/1998 | Chen et al. |
| 5,766,234 | A | 6/1998 | Chen et al. |
| 5,782,896 | A | 7/1998 | Chen et al. |
| 5,814,008 | A | 9/1998 | Chen et al. |
| 5,827,186 | A | 10/1998 | Chen et al. |
| 5,830,526 | A | 11/1998 | Wilson et al. |
| 5,865,840 | A | 2/1999 | Chen |
| 5,997,569 | A | 12/1999 | Chen et al. |
| 6,080,160 | A | 6/2000 | Chen et al. |
| 6,096,066 | A | 8/2000 | Chen et al. |
| 6,210,425 | B1 | 4/2001 | Chen |
| 6,238,426 | B1 | 5/2001 | Chen |
| 6,273,904 | B1 | 8/2001 | Chen et al. |
| 6,281,611 | B1 | 8/2001 | Chen et al. |
| 6,319,273 | B1 | 11/2001 | Chen et al. |
| 6,331,744 | B1 | 12/2001 | Chen et al. |
| 6,344,050 | B1 | 2/2002 | Chen |
| 6,416,531 | B2 | 7/2002 | Chen |
| 6,454,789 | B1 | 9/2002 | Chen et al. |
| 6,520,669 | B1 | 2/2003 | Chen et al. |
| 6,580,228 | B1 | 6/2003 | Chen |
| 7,018,395 | B2 | 3/2006 | Chen |
| 7,288,106 | B2 | 10/2007 | Heacock et al. |
| 7,320,786 | B2 | 1/2008 | Chen |
| 7,511,031 | B2 | 3/2009 | Chen |
| 7,802,572 | B2 | 9/2010 | Hahne |
| 8,057,464 | B2 | 11/2011 | Chen et al. |
| 8,226,946 | B2 | 7/2012 | Chen |
| 8,450,359 | B2 | 5/2013 | McCoy et al. |
| 8,685,005 | B2 | 4/2014 | Dahm et al. |
| 8,685,071 | B2 | 4/2014 | Burwell et al. |
| 8,759,092 | B2 | 6/2014 | Goodrich |
| 9,149,651 | B2 | 10/2015 | Keltner et al. |
| 9,278,148 | B2 | 3/2016 | Fewkes et al. |
| 9,527,918 | B2 | 12/2016 | Fiori et al. |
| 10,307,610 | B2 | 6/2019 | Keltner et al. |
| 2003/0114434 | A1 | 6/2003 | Chen et al. |
| 2006/0223729 | A1 | 10/2006 | Hamblin et al. |
| 2007/0038204 | A1 | 2/2007 | Chen et al. |
| 2007/0059316 | A1 | 3/2007 | Pallenberg et al. |
| 2007/0059791 | A1 | 3/2007 | Goodrich |
| 2007/0129776 | A1 | 6/2007 | Robins et al. |
| 2007/0133935 | A1 | 6/2007 | Fine |
| 2007/0142880 | A1 | 6/2007 | Barnard et al. |
| 2007/0286878 | A1 | 12/2007 | Harruna |
| 2008/0015189 | A1 | 1/2008 | Hamblin |
| 2008/0107636 | A1* | 5/2008 | Goodrich ............ A61M 1/0213 424/93.72 |
| 2009/0317436 | A1 | 12/2009 | Wilson et al. |
| 2010/0241054 | A1 | 9/2010 | Dacey, Jr. et al. |
| 2010/0274330 | A1 | 10/2010 | Burwell et al. |
| 2010/0305436 | A1 | 12/2010 | Chen et al. |
| 2011/0008372 | A1 | 1/2011 | Chen |
| 2011/0009464 | A1 | 1/2011 | Chen |
| 2011/0014239 | A1 | 1/2011 | Goodrich |
| 2011/0110818 | A1 | 5/2011 | Mowbray-d'Arbela et al. |
| 2012/0100039 | A1 | 4/2012 | Appeaning et al. |
| 2012/0209359 | A1 | 8/2012 | Chen et al. |
| 2014/0052050 | A1 | 2/2014 | Courtin |
| 2014/0303547 | A1 | 10/2014 | Loupis et al. |
| 2016/0091399 | A1 | 3/2016 | Chen et al. |
| 2016/0193338 | A1 | 7/2016 | Loupis et al. |
| 2016/0220728 | A1 | 8/2016 | Adams et al. |
| 2016/0270895 | A1* | 9/2016 | Zoll ............ A61B 18/18 |
| 2017/0056603 | A1 | 3/2017 | Cowan et al. |
| 2018/0099063 | A1 | 4/2018 | Lyons et al. |
| 2018/0243790 | A1* | 8/2018 | Grossman ............ B05D 7/52 |
| 2019/0161562 | A1 | 5/2019 | Bakar et al. |
| 2019/0314502 | A1 | 10/2019 | Wei |
| 2020/0315280 | A1* | 10/2020 | Kaye ............ A42B 3/20 |

FOREIGN PATENT DOCUMENTS

| | | |
|---|---|---|
| CA | 2537235 A1 | 1/2005 |
| CN | 104589717 B | 3/2017 |
| CN | 208597758 U | 3/2019 |
| EP | 1644082 A2 | 4/2006 |
| EP | 1684865 A1 | 8/2006 |
| WO | 98/32494 A1 | 7/1998 |
| WO | 1999/49823 A1 | 10/1999 |
| WO | 2004/108249 A1 | 12/2004 |
| WO | 2005032459 A2 | 4/2005 |
| WO | 2006086770 A2 | 8/2006 |
| WO | 2008046019 A1 | 4/2008 |
| WO | 2014/130740 A1 | 8/2014 |
| WO | 2018/022926 A1 | 2/2018 |
| WO | 2019/183320 A1 | 9/2019 |

OTHER PUBLICATIONS

Naito, K. et al. "Single-molecule detection of airborne singlet oxygen," Journal of the American Chemical Society 128 (51): p. 16430-16431, Nov. 30, 2006.

Ogilby, P. R. "Singlet oxygen: There is indeed something new under the sun," Chemical Society reviews 39(8): pp. 3181-3209, Jun. 22, 2010.

Zhao, Y. et al. "Singlet oxygen generation on porous superhydrophobic surfaces: Effect of gas flow and sensitizer vetting on trapping efficiency," The Journal of Physical Chemistry A 118(45): pp. 10364-10371, 2014.

Gao, R. et al. "Nano-photosensitizer based on layered double hydroxide and isophthalic acid for singlet oxygenation and photodynamic therapy," Nature communications 9(1):2798, pp. 1-10, 2018.

Felgenträger, A., et al. "Singlet oxygen generation in porphyrin-doped polymeric surface coating enables antimicrobial effects on *staphylococcus aureus*," Physical Chemistry Chemical Physics:PCCP, 16(38): pp. 20598-20607, Aug. 7, 2014.

Pushalkar, S. et al. "Superhydrophobic photosensitizers: Airborne 1O2 killing of an in vitro oral biofilm at the plastron interface," ACS Applied Materials & Interfaces 10(30): pp. 25819-25829, Jul. 4, 2018.

Hwang, J. et al. "Study of singlet oxygen dynamics on silicon polymer matrix," Journal of Analytical Methods in Chemistry vol. 2019 Article ID 2584686, pp. 1-6, Feb. 19, 2019.

Bartusik, D. et al. "Bacterial inactivation by a singlet oxygen bubbler: Identifying factors controlling the toxicity of 1O2 bubbles," Environmental Science & Technology 46(21): pp. 12098-12104, Oct. 18, 2012.

Aebisher, D. et al. "Superhydrophobic surfaces as a source of airborne singlet oxygen through free space for photodynamic therapy," ACS Applied Bio Materials 3(4): pp. 2370-2377, Mar. 17, 2020.

Plotino, G., et al. "Photodynamic therapy in endodontics," International Endodontic Journal (52): pp. 760-774, 2019.

Meller, D., et al. "Photodisinfection Therapy: Essential Technology for Infection Control," <https://infectioncontrol.tips/2020/01/17/photodisinfection-therapy/> [retrieved Jul. 30, 2020], 20 pages.

Boyce, J.M., "Modern technologies for improving cleaning and disinfection of environmental surfaces in hospitals," ©2016 <https://www.ncbi.nlm.nih.gov/pmc/articles/PMC4827199/> [retrieved Jul. 30, 2020], 20 pages.

(56) References Cited

OTHER PUBLICATIONS

"What is Photodisinfection?," Ondine Biomedical, <https://ondinebio.com/technology> [retrieved Aug. 12, 2020], 5 pages.
International Search Report and Written Opinion dated Nov. 30, 2021, in International Application PCT/US2021/0046417, filed Aug. 18, 2021, 11 pages.
International Search Report and Written Opinion dated Dec. 6, 2021, in International Application PCT/US2021/046722, filed Aug. 19, 2021, 9 pages.
International Search Report and Written Opinion dated Nov. 8, 2021, issued in International Application No. PCT/US2021/046416, filed Aug. 18, 2021, 9 pages.
Chen, James, et al., "Disinfection Method and Apparatus," U.S. Appl. No. 17/405,900, filed Aug. 18, 2021, 55pages.
Chen, James, et al., "Photosensitizer Combination," U.S. Appl. No. 17/463,245, filed Aug. 31, 2021, 46 pages.
Chen, James, et al., "Invisible Singlet Film," U.S. Appl. No. 17/389,936, filed Jul. 30, 2021, 33 pages.
Chen, James, et al., "Vaccine Generation," U.S. Appl. No. 17/244,610, filed Apr. 29, 2021, 19 pages.
Marcus, P. et al. "In vitro analysis of virus particle subpopulations in candidate live-attenuated influenza vaccines distinguishes effective from ineffective vaccines," Journal of Virology 84(21): pp. 10974-10981, Nov. 2010.
Seghatchian, J_ et al. "Main properties of the THERAFLEX MB-plasma system for pathogen reduction," Transfusion Medicine and Hemotherapy 38(1): pp. 55-64, 2011.
Almeida, A., et al. "Phage Therapy and Photodynamic Therapy: Low Environmental Impact Approaches to Inactivate Microorganisms in Fish Farming Plants," Marine Drugs 7(3): pp. 268-313, 2009.
Hasenleitner, M., et al. "In the Right Light: Photodynamic Inactivation of Microorganisms Using a LED-Based Illumination Device Tailored for the Antimicrobial Application," Antibiotics 9(1 ): pp. 1-13, 2020.
Trempolec, N., et al. "Photodynamic Therapy-Based Dendritic Cell Vaccination Suited to Treat Peritoneal Mesothelioma." Cancers 12.3 (2020): 545.
Mertes, P., et al. "Methylene blue-treated plasma: an increased allergy risk?" The Journal of Allergy and Clinical Immunology 130(3): pp. 808-812, 2012.
Henneberry, B. How Surgical Masks are Made. Thomas Industry. <https://www.thomasnet.com/articles/other/how-surgical-masks-are-made/>[Accessed Mar. 21, 2020], 1 page.
Clear Polypropylene Omnexus: The material selection platform. <https://omnexus.specialchem.com/centers/clear-polypropylene> [Accessed Mar. 21, 2020], 1 page.
Weaver, E.A. "Dose Effects of Recombinant Adenovirus Immunization in Rodents," Vaccines 7(4):144 pp. 1-11, 2019.
Hankaniemi, M.M., et al. "A comparative study of the effect of UV and formalin inactivation on the stability and Immunogenicity of a coxsackievirus B1 vaccine," Vaccine 37: pp. 5962-5971, 2019.
Mills, D., et al. "Ultraviolet germicidal irradiation of influenza-contaminated N95 filtering facepiece respirators," AJIC: American Journal of Infection Control 46(7): pp. e49-e55, 2018.
Bull, J.J., et al. "Transmissible Viral Vaccines," Trends in Microbiology 26(1): pp. 6-15, Jan. 2018.
Barrett, P.N., et al. "Vero cell technology for rapid development of inactivated whole virus vaccines for emerging viral diseases," Expert Review of Vaccines 16(9): pp. 883-894, 2017.
Klasse, P.J. "Molecular determinants of the ratio of inert to infectious virus particles," Progress in Molecular Biology and Translational Science 129: pp. 285-326, 2015.
Klausberger, M. et al. "One-shot vaccination with an insect cell-derived low-dose influenza A H7 virus-like particle preparation protects mice against H7N9 challenge," Vaccine 32(3): pp. 355-362, 2014.
Quan, F. et al. "Dose sparing enabled by skin immunization with influenza virus-like particle vaccine using microneedles," Journal of Controlled Release 147(3): pp. 326-332, 2010.
Victoria, J_ et al. "Viral nucleic acids in live-attenuated vaccines: Detection of minority variants and an adventitious virus," Journal of Virology 84(12): pp. 6033-6040, Jun. 2010.
Maves, R. et al. "Immunogenicity of a psoralen-inactivated dengue virus type 1 vaccine candidate in mice." Clinical and Vaccine Immunology 17(2): pp. 304-306, Feb. 2010.
Prausnitz, M.R., et al. "Microneedle-based vaccines," Current Topics in Microbiology and Immunology 333: pp. 369-393, 2009.
Geeraedts, F., et al. "Superior immunogenicity of inactivated whole virus H5N 1 influenza vaccine is primarily controlled by toll-like receptor signalling," PLoS Pathogens 4(8): p. e1000138, Aug. 2008.
Monath, T.P. et al. "A live, attenuated recombinant west nile virus vaccine," Proceedings of the National Academy of Sciences, USA 103(17): pp. 6694-6699, Apr. 25, 2006.
Meurice, F. et al. "Immunogenicity and safety of a live attenuated varicella vaccine (oka/SB bio) in healthy children," The Journal of Infectious Diseases 174(Supplement 3): pp. S324-S329, Nov. 1996.
THERAFLEX-MB Plasma-Processing Principle, advertisement published by MacoPharma, Sep. 2007.
"Influenza Vaccine," Cytiva, https://www.gelifesciences.com/en/us/solutions/bioprocessing/knowledge-center/influenza, vaccine-manufacturing [retrieved Mar. 30, 2020], 10 pages.
Borkar, T.G., et al. "Techniques Employed in Production of Traditional Vaccines Commonly Used by Military Forces: A Review," Journal of Archives in Military Medicine 7(102):e96149, pp. 1-12, Jun. 2019.
Dancer, Stephanie J. "Controlling hospital-acquired infection: focus on the role of the environment and new technologies for decontamination." Clinical microbiology reviews 27.4 (2014): 665-690.
Pyrek, K. "Portable medical equipment: A significant source of transmission," Feb. 1, 2018, 16 pages.
Russotto, V., Cortegiani, A., Raineri, S. M., & Giarratano, A. Bacterial contamination of inanimate surfaces and equipment in the intensive care unit. Journal of Intensive Care. 2015;3(1):54, pp. 1-8.
Gabriele Messina, Emma Ceriale, Daniele Lenzi, Sandra Burgassi, Elena Azzolini, Pietro Manzi. Environmental contaminants in hospital settings and progress in disinfecting techniques. BioMed research international. 2013;2013:429780, 8 pages.
Bonetta S, Bonetta S, Motta F, Strini A, Carraro E. Photocatalytic bacterial inactivation by TiO2-coated surfaces. AMB Expr. 2013;3(1):1-8. https://www.ncbi.nlm.nih.gov/pubmed/24090112. doi: 10.1186/2191-0855-3-59.
Air permeable(breathable) film, <http://tamstech.net> [Accessed Mar. 25, 2020], 1 page.
Siracusa, Valentina. "Food packaging permeability behaviour: A report." International Journal of Polymer Science 2012 (2012), 2 pages.
Makdoumi K, Hedin M, Backman A. Different photodynamic effects of blue light with and without riboflavin on methicillin-resistant staphylococcus aureus (MRSA) and human keratinocytes in vitro. Lasers Med Sci. 2019;34(9):1799-1805.
Kino, K., et al. Commentary on the phototoxicity and absorption of vitamin B2 and its degradation product, lumichrome. Pharmaceutica analytica acta. 2015;6(8) doi: 10.4172/2153-2435. 1000403.
Koshi E, Mohan A, Rajesh S, Philip K. Antimicrobial photodynamic therapy: An overview. Journal of Indian Society of Periodontology. 2011;15(4):323-327, 1 page.
Bhat M, Acharya S, Prasad K, Kulkarni R, Bhat A, Bhat D. Effectiveness of erythrosine-mediated photodynamic antimicrobial chemotherapy on dental plaque aerobic microorganisms: A randomized controlled trial. Journal of Indian Society of Periodontology. 2017;21(3):210-215.
Lee Y, Park H, Lee J, Seo H, Lee S. The photodynamic therapy on streptococcus mutans biofilms using erythrosine and dental halogen curing unit. International journal of oral science 2012;4(4):196-201.
Fracalossi C, Nagata JY, Pellosi DS, et al. Singlet oxygen production by combining erythrosine and halogen light for photodynamic inactivation of streptococcus mutans. Photodiagnosis and Photodynamic Therapy. 2016;15:127-132. https://search.datacite.org/works/10.1016/j.pdpdt.2016.06.011. doi: 10.1016/j.pdpdt.2016.06.011, 1 page.

(56) References Cited

OTHER PUBLICATIONS

Wood S, Metcalf D, Devine D, Robinson C. Erythrosine is a potential photosensitizer for the photodynamic therapy of oral plaque biofilms. Journal of antimicrobial chemotherapy. 2006;57(4):680-684.

Gahleitner, Markus, et al. Sterilization effects on polypropylene: technology and polymer type effects., Jan. 2003, <https://www.researchgate.net/publication/288596501>, 3 pages.

"Cover Picture: Optik & Photonik Apr. 2015," Abstract, vol. 10, Issue 4, 2015,<https://doi.org/10.1002/opph.201590064>, 2 pages.

Molitch-Hou, M., "First 3D Printed Fiber Optics Created by University of Sydney researchers with Desktop 3d Printer," 2015, 3D Printing Industry, The Authority on Additive Manufacturing, <https://3dprintingindustry.com/news/first-3d-printed-fiber-optics-createdby-university-of-sydney-researchers-with-desktop-3d-printer-55047/> [Accessed Mar. 24, 2020], 1 page.

Ismail, Salim, et al. "Efficacy of a novel light-activated antimicrobial coating for disinfecting hospital surfaces." Infection Control & Hospital Epidemiology 32.11 (2011): 1130-1132.

Lee, Im-Soon, et al. "Aerosol particle size distribution and genetic characteristics of aerosolized influenza A H1N1 virus vaccine particles." Aerosol and Air Quality Research 11.3 (2011): 230-237.

Meyer, Michelle, et al. "Aerosolized Ebola vaccine protects primates and elicits lung-resident T cell responses." The Journal of clinical investigation 125.8 (2015): 3241-3255.

Noimark, Sacha, et al. "Incorporation of methylene blue and nanogold into polyvinyl chloride catheters; a new approach for light-activated disinfection of surfaces." Journal of Materials Chemistry. 2012; 22(30): 15388-15396. <https://doi.org/10.1039/C2JM31987J>, 1 page.

Noimark, Sacha, Elaine Allan, and Ivan P. Parkin. "Light-activated antimicrobial surfaces with enhanced efficacy induced by a dark-activated mechanism." Chemical Science 5.6 (2014): 2216-2223.

Piccirillo, Clara, et al. "Antimicrobial activity of methylene blue and toluidine blue O covalently bound to a modified silicone polymer surface." Journal of Materials Chemistry 19.34 (2009): 6167-6171.

Fecht, S., "The First Fully 3-D Printed LEDs Are Here," 2014, <https://www.popsci.com/article/technology/first-fully-3-d-printed-leds-are-here/> [Accessed Mar. 24, 2020], 8 pages.

Waldman, Robert H., John J. Mann, and Parker A. Small. "Immunization against influenza: prevention of illness in man by aerosolized inactivated vaccine." Jama 207.3 (1969): 520-524 doi:10.1001/jama.1969.03150160032007, 1 page.

International Search Report and Written Opinion dated Feb. 2, 2022, issued in International Application No. PCT/US2021/046419, filed Aug. 18, 2021, 11 pages.

International Search Report and Written Opinion dated Feb. 1, 2022, issued in International Application No. PCT/US2021/048444, filed Aug. 31, 2021, 14 pages.

\* cited by examiner

ANTIMICROBIAL PREVENTIVE NETTING

CROSS-REFERENCE TO RELATED APPLICATION

This application claims the benefit of U.S. Provisional Application No. 63/073,652, filed on Sep. 2, 2020, herein expressly incorporated by reference in its entirety.

BACKGROUND

Social distancing as a means of reducing spread of infections is highly recommended and can be enforced by laws during viral epidemics and pandemics. Social distancing implies a minimum separation between two persons of at least six feet or two meters due to studies demonstrating reduced risk of inhalation or bodily contamination due to exhaled microbial laden droplets. Droplets tend to fall to the ground with gravity, and at least in still air conditions, the six foot or two meter distance is believed to be at least somewhat protective in this regard. However, other studies have demonstrated the ability of microbial droplets and aerosolized microbial particles not in droplets to travel much greater distances if coughed, sneezed, or otherwise forcibly expelled. Also, in ambient windy outdoor conditions or where active air circulation is occurring indoors, microbial laden droplets such as airborne viral particles can travel much further, with heightened risk of contamination of persons, and the surfaces of objects in the environment beyond six feet or two meters. Social distancing may be inconvenient, problematic, or impossible in many situations such as in crowds attending events, workplaces, schools, on public transportation, in commercial aircraft, while participating in team sports, at home or in public institutions and venues, and the like. Typical facemasks that may be worn by the public that are homemade or purchased (public facemasks) are usually not the highly protective respirators of the N95 type, due to respirator shortages and the fact that these types of respirators are uncomfortable, require special training for use, and are therefore largely worn only by healthcare workers.

However, public facemasks may not be tolerable for some individuals who have respiratory problems, who feel claustrophobic wearing them, or have difficulty communicating while wearing a public facemask.

Plastic or plexiglass types of screens are also utilized with the goal of providing some protection for workers in check-out lines, and in other settings where workers are relatively stationary, and where screens can be fixed in place to provide a barrier between the worker and other individuals in the vicinity. Unfortunately, these types of screen setups are not feasible or are impractical in many workplaces, event and various public settings such as restaurants, movie theaters, parks, beaches, eating establishments, schools, music and sports events, while waiting in lines, on all forms of public transport, while flying in aircraft, on cruise ships, and the like.

Clearly, there is an unmet need for an alternative form of antimicrobial protection which can more easily be utilized where social distancing is not feasible, may be more socially acceptable, and that can be worn by children, and that can be utilized more easily and widely wherever relatively close person to person contact occurs.

SUMMARY

Generally, disclosed herein are embodiments of antimicrobial preventive netting. In some embodiments, the antimicrobial preventive netting is used as headgear to protect against viral contamination.

In some embodiments, antimicrobial preventive netting is configured to fit over headgear, such as a baseball hat or a sunhat with a brim, or even a helmet.

In some embodiments, the antimicrobial preventive netting incorporates an elastic band which fits over the headgear and is in contact just above and resting on the brim or headgear rim.

In some embodiments, the lower border of the antimicrobial preventive netting can be loose, fastened, or tucked into a garment around the shoulders or torso.

In some embodiments, the antimicrobial preventive netting is held in a circular configuration around the face and head around the by a thin wire spring which may be metal or polymeric, which is incorporated into the netting such that it is horizontal in orientation, and serves to hold the netting open around the face and neck.

In some embodiments, the antimicrobial preventive netting includes electret netting material to enhance viral particle capture and filtration In some embodiments, the antimicrobial preventive netting includes optically transparent or translucent netting material.

In some embodiments the antimicrobial preventive netting is semi-transparent or nontransparent netting material.

In some embodiments, the antimicrobial preventive netting can be machine washable and reusable, or single-use disposable.

In some embodiments, the antimicrobial preventive netting can include a device such as a home electret charger for generating electric charges on the netting.

In some embodiments, an at-home container or canister filled with a photosensitizer based solution may be used for reapplication of the one or more photosensitizers to the antimicrobial preventive netting.

In some embodiments, the container or canister can be tumbled by hand or automatically by way of a small incorporated motor to disperse the photosensitizing solution evenly on the antimicrobial preventive netting.

Tumbling the container or canister by rotating it electrically charges the antimicrobial preventive netting material, which adds to the filtration, capture, and retention of oppositely electrically charged microbial particles and/or droplets.

The container or canister is comprised of a material such as a metal that enables the triboelectric effect to impart a charge to the antimicrobial preventive netting.

In some embodiments, the antimicrobial preventive netting is deployable as a temporary, portable barrier which can be set up on demand by average users, quickly, conveniently, with no special tools, and no special training.

In some embodiments, the antimicrobial preventive netting is configurable into one or more interlocking vertical or horizontal screens, or can be in the shape of a dome, cone, sphere, pyramid, tube, cube, cuboid, tent, or cylinder, surrounding or shielding the user on at least one side, or completely covering all sides of the user.

In some embodiments, the one or more photosensitizers can be applied to the antimicrobial preventive netting, such as via a spray-on solution, applied as a gel, brushed or swabbed on, or the netting can be dipped or soaked in a container incorporating a solution that includes one or more photosensitizers.

In some embodiments, the antimicrobial preventive netting has the advantage that no material touches the face of a user, so the netting may be worn comfortably.

In some embodiments, the antimicrobial preventive netting has the advantage of allowing normal respiration, since there is no resistance to airflow.

In some embodiments, the antimicrobial preventive netting may be transparent so that facial recognition and a normal volume for voice communication is maintained.

In some embodiments, the antimicrobial preventive netting has the advantage of allowing normal behavior and modes of eating, ingestion of medications, and drinking of fluids, by providing access by reaching under the netting.

In some embodiments, the antimicrobial preventive netting has the advantage that claustrophobia is reduced compared to public facemasks.

In some embodiments, the antimicrobial preventive netting has the advantage of incorporating an ambient light activated photosensitizing solution that enables an active antimicrobial preventive function in addition to the physical barrier function, and in doing so, provides two way protection for the user in contradistinction to the public facemask so that the user benefits from enhanced protection from other potentially infected individuals, and other persons near the user are protected to a greater degree when the user is potentially infected.

In some embodiments, methylene blue is used as a photosensitizer and is positively charged which aids in attracting and retaining negatively charged microbial particles for photodynamic inactivation.

In some embodiments, antimicrobial preventive netting has the advantage that wearing the netting away from the face of a user can be more acceptable and safer when the user is a child.

In some embodiments, the antimicrobial preventive netting can be deployed in virtually any public situation.

In some embodiments, the antimicrobial preventive netting enables being safer when in close proximity to other individuals and reduces the need for social distancing when it is not desirable or feasible in any case.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to any measurements "about" means+/−5%.

It shall be understood that the term "microbial", as used herein refers to an infectious microorganism, pathogen, or agent, including one or more of a virus, viroid, bacterium, archaea, protists, protozoan, prion, fungus, toxin, or the like.

Also, it shall be understood that the term "immunogen", as used herein refers to an antigen or any other substance that induces both an immune response by a patient's immune system and generation of antibodies that bind to the immunogen.

Figure 1:
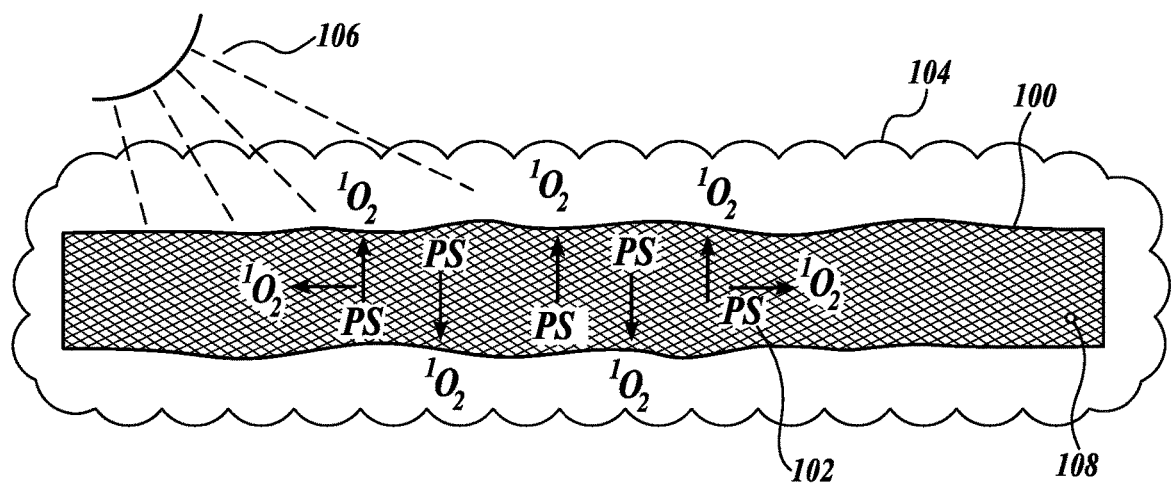
FIG. 1 is a diagrammatical illustration of antimicrobial preventive netting containing a photosensitizer according to one embodiment.

With reference to FIG. 1, antimicrobial preventive netting 100 is illustrated having at least one photosensitizer 102 absorbed into the fibers or threads of the netting 100 or on the exterior surfaces of the netting 100. When either natural or artificial light 106 is absorbed by the photosensitizer 102, singlet oxygen is generated that diffuses out from and in proximity to the netting 100 to form a layer or cloud 104 of singlet oxygen at a concentration sufficient to inactivate viruses and other pathogens that come within the singlet oxygen layer 104.

Singlet oxygen is known by the chemical formula, $^1O_2$. Singlet oxygen is a reactive species, though the decay at ambient temperature is considered slow. In one embodiment, the antimicrobial preventive netting 100 contains an amount of one or more photosensitizers 102, wherein the amount of the one or more photosensitizers is capable of generating the cloud 104 of virucidal singlet oxygen on both sides of the netting with a maximum depth of the singlet oxygen less than 0.7 centimeters from the netting surface, wherein the cloud is generated by the reaction of the one or more photosensitizers with the ambient light 106. In one embodiment, the cloud 104 of singlet oxygen can extend to a depth of at least 1 centimeter.

In one embodiment, the antimicrobial preventive netting 100 contains an effective amount of one or more photosensitizers 102. The effective concentration range of the one or more photosensitizers can be from 0.05 μM to 1000 μM, and any included range, such as concentration ranges of 0.05 μM to 0.5 μM, 0.5 μM to 5 μM, 5 μM to 50 μM, 50 μM to 100 μM, 100 μM to 500 μM, 500 μM to 1000 μM, wherein the one or more photosensitizers 102 are contained within the netting 100 or on exterior surfaces of the netting. In one embodiment, an effective amount of the one or more photosensitizers is an amount capable of providing a cloud of singlet oxygen to a depth of at least one centimeter from an exterior surface of the netting 100 when at least 100 lux of light photoactivates the one or more photosensitizers 102 for at least 60 minutes or more.

In some embodiments, the photosensitizer 102 or combination of photosensitizers includes, but is not limited to, all types of methylene blue derivatives and methylene blue itself, xanthene dyes and derivatives, chlorophyll derivatives, tetrapyrrole structures, porphyrins, chlorins, bacteriochlorins, phthalocyanines, texaphyrins, prodrugs such as aminolevulinic acids, phenothiaziniums, squaraine, boron compounds, various transition metal complexes, hypericin, riboflavin, curcumin, titanium dioxide, psoralens, tetracyclines, flavins such as riboflavin, riboflavin derivatives, erythrosine, erythrosine derivatives, and the like. In some embodiments, a combination of two or more photosensitizers are used.

In some embodiments, preferred photosensitizers 102 are generally recognized as safe and are capable of absorbing light over a wide spectral range, such as erythrosine, methylene blue, and riboflavin. In some embodiments, the photosensitizers are capable of application to the netting 100 by the end user of the antimicrobial preventive netting. For this purpose, in some embodiments, the specific photosensitizers, methylene blue, erythrosine, and riboflavin can be provided in a powder form or in an aqueous solution containing saline or plain water or can be supplied in a gel formulation for application to the netting.

In the powder form, the photosensitizer or combination of photosensitizers is brushed onto the netting surface or the powder is solubilized in an aqueous or hydrophilic solution and then applied to the netting surface by means of an applicator or applied with a brush or by dipping the netting into a container of the photosensitizer solution. The specific concentrations of each photosensitizer are optimized in laboratory testing where singlet oxygen is output into a solution or into air is measured, with the goal being to maximize singlet oxygen output for a useful length of time, for example for 4 to 24 hours after a single application episode. In some embodiments, the percent by weight of any photosensitizer in a combination of photosensitizers is in the range from 1% by weight up to 99% by weight or any value in between based on the total weight of only the photosensitizers.

In some embodiments, the netting 100 can be a thin fabric, cloth, or film having a much smaller thickness compared to the length and width dimension. In some embodiments, the netting 100 can be loose, such that the netting 100 can be draped over a person's head or connected to headgear or draped over a rigid framework to create an enclosure. In some embodiments, the netting 100 can be a thin yet rigid or semi-rigid material that can support itself without the need for stiffening or supporting rods. In some embodiments, the netting 100 is a loose material, but, is configured to be supported by the addition of support members.

In some embodiments, the netting 100 includes an arrangement of holes 108 in rows and columns. The holes traverse the netting 100 completely through and across the thickness of the netting. In some embodiments, the holes can be randomly distributed throughout the netting 100. In some embodiments, the holes 108 can be created by weaving or otherwise interconnecting fibers or threads running in one of two distinct directions such that fibers placed in one direction are spaced apart, and the fibers placed in the second direction are also spaced apart, thereby creating the holes 108 defined by a boundary between the two fibers in the first direction two fibers in the second direction. In some embodiments, the holes 108 can be created by micro-punching a sheet or any thin material either via a mechanical punch or laser. In some embodiments, the holes 108 can be created through the use of casting films or sheets with soluble particulate poragens and then dissolving the poragens. In some embodiments, the number of holes 108 and the size of the holes 108 allows the netting 100 to be sufficiently transparent to allow a person to visibly perceive their surroundings through the netting. Similarly, persons will be able to recognize facial features of the person behind the netting. In some embodiments, the netting 100 can be semi-transparent or completely opaque. The netting 100 is also sufficiently porous to allow breathing with little or any resistance to airflow. The hole 108 shape and size can be circular, oblong, rectangular, square, or any combination thereof.

In some embodiments, individual hole 108 diameter or longest side dimension or gaps in the fiber configuration in the fabric ranges from 10 to 200,000 nanometers, and included ranges, for example, 10 to 160 nanometers, 160 nanometers to 1000 nanometers, 1000 nanometers to 200,000 nanometers. Air gaps can be provided in the network or meshwork of elongate microfibrils, microfibers, or nanofibers which is optimized for microbial laden droplet capture, microbial particle capture, and fabric breathability by testing in a laboratory, using known filtration and related air passage techniques as standardized by the U.S. National Institute for Occupational Safety and Health (NIOSH).

In some embodiments, the netting 100 is made from polymeric materials such as polypropylene, polyvinyl chloride and alcohols, polyimides, polyethylene, nylon, polyester, cotton, fiberglass, various metals manufactured as a mesh, various nanomaterial fibers, ceramic fibers, rayons, silk, polyacrylonitrile, which may or may not incorporate metallic or other types of coatings which impart electret properties, and hydrophobicity, and are able to withstand multiple washings in a standard washing machine.

Any type of light source 106, including sunlight, ambient light, and/or artificial light, can be used that emits the proper wavebands or wavelengths of light that are effectively absorbed by the photosensitizers to cause singlet oxygen generation. The illumination time and intensity of light needed for adequate microbial disinfection of the netting by a cloud of generated singlet oxygen may be determined empirically, experimentally, and/or derived from known data. In some embodiments, the light source can be comprised of light emitting diodes (LED), xenon lamps, fluorescent bulbs and tubes, incandescent light bulbs, electroluminescent devices, lasers, and the like, even including sunlight. Other known or contemplated light sources are not excluded in any fashion, and include all known wavelengths and wavebands known to lead to a photodynamic effect that generates singlet oxygen which is particular to the photosensitizer or combinations of different types and amounts of photosensitizers.

Figure 2:
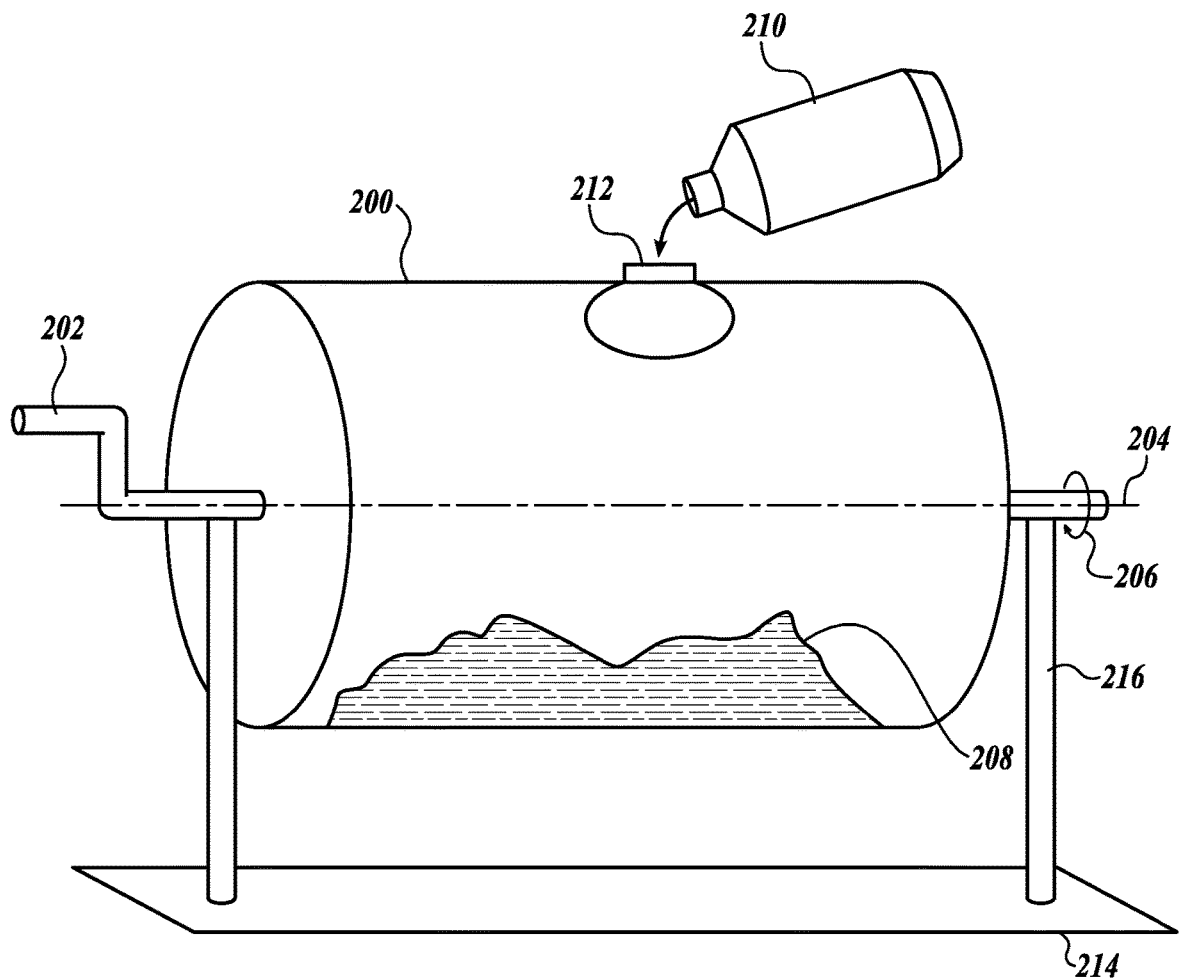
FIG. 2 is a diagrammatical illustration of a container for applying a photosensitizer onto antimicrobial preventive netting according to one embodiment.

Referring to FIG. 2, in some embodiments, the application of one or more photosensitizers to the netting is made by a coating or wetting technique that can be performed at home using a hand-operated container 200. Container 200 is shown as a cylinder in a horizontal position incorporating a hand crank 202 which rotates the container 200 around axis 204 in the direction of arrow 206 which tumbles netting 208 residing inside the container 200. The container 200 incorporates a watertight door 212 which opens by way of a hinge or is screwed on and maintains a watertight seal which prevents leakage. Photosensitizer solution is contained in bottle 210 and can be poured through an orifice after unsealing the door 212. The container 200 can be supported and stabilized on a platform 214 with supports 216 extending upwards from the platform 214 that are attached to axles extending from the ends of the container 200 which enables rotation of container 200 around the horizontal axis 204 through the hand crank 202. The hand crank 202 incorporated into the side of the container 200 enables a manually driven rotating movement to aid in dispersing the added photosensitizer solution evenly to the netting 208 surface.

In another embodiment, a motor in place of the hand crank 202 is connected to the container 200 for automating rotation and providing an adjustable or fixed rotation speed. In both the hand crank and motor rotated container embodiments, the netting is tumbled in a fashion adequate to coat the net with an effective amount of photosensitizer solution.

The photosensitizing solution is comprised of any of the aforementioned photosensitizers. In some embodiments, the photosensitizer solution can include one or more of medical or laboratory grade methylene blue, food grade erythrosine dye, and food grade riboflavin, in various concentrations, in various aqueous solutions which are safe for ingestion, or in a powder formulation. In some embodiments, the aqueous or powder photosensitizer formulation is supplied with the container and is used as a refill prior to each netting treatment.

The technique of applying photosensitizer solution onto netting 208 can be scaled up or down according to the intended application of the netting. In some embodiments, netting 208 is used on a small scale for single items of personal protective equipment (PPE). In some embodiments, netting 208 is of a larger scale to create enclosures surrounding an entire person or groups of persons.

In some embodiments, the container 200 is made from a light blocking polymeric or plastic material. In some embodiments, the dimensions of container 200 can range from 6 inches long by 3 inches in diameter to a 2 meter long and 1 meter diameter container. Other dimensions and various shapes of containers other than a cylinder can be used. The size of the container 200 will be determined by various testable factors such as the volume of netting to be treated with at least one photosensitizer and the ability of the container to electrically charge the netting. In any event, the dimensions of the container 200 can be large enough to accommodate one or more than one individual netting.

In some embodiments, the container 200 is comprised of a metal which induces a triboelectric effect, which electrically charges the netting 208 as the container 200 is rotated during photosensitizer application, which occurs separately, or simultaneously to the electrically charging process. The netting 208 can be made from electret materials to allow charging the netting more readily. Electret materials may include synthetic polymers, including, but not limited to, fluoropolymers, polypropylene, polyethyleneterephthalate, and the like. An electret material is any known material that can be charged and retains its electric polarization (positive or negative).

The antimicrobial preventive netting illustrated in FIG. 1 has many applications including for use as personal protective equipment against viruses and other pathogens.

Figure 3:
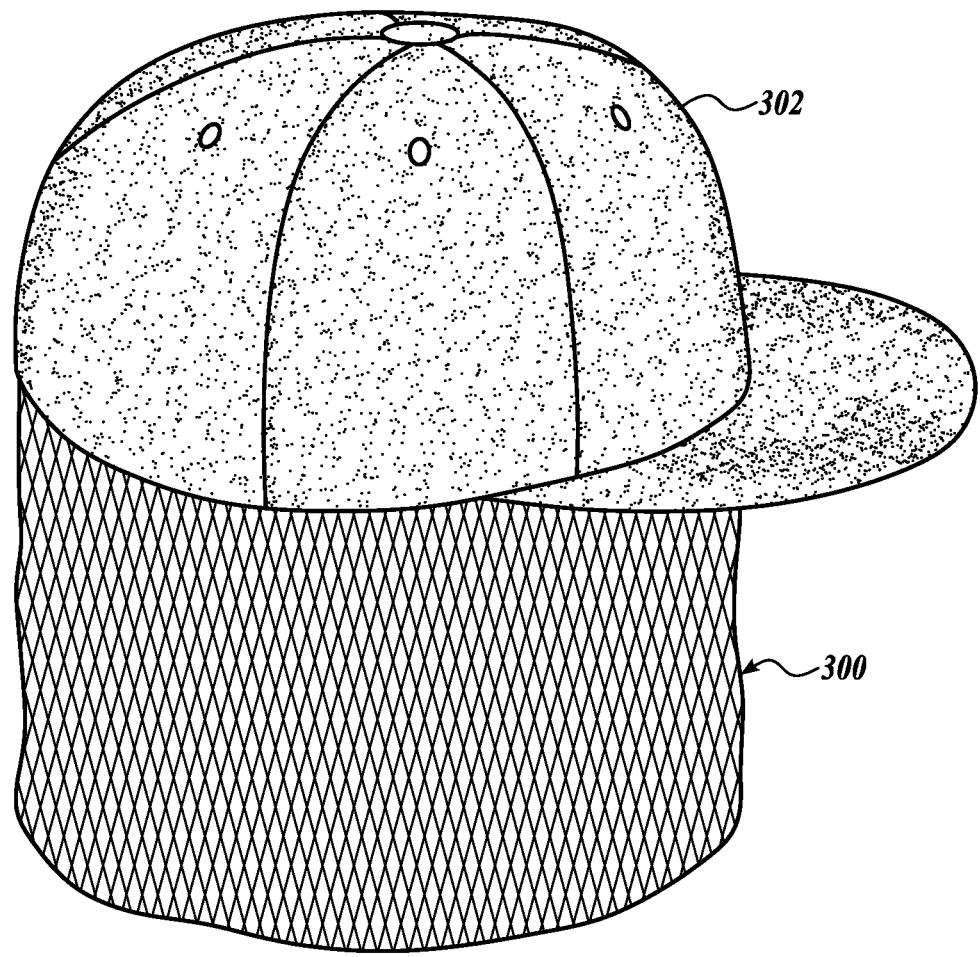
FIG. 3 is a diagrammatical illustration of headgear including antimicrobial preventive netting according to one embodiment.

FIG. 3 shows an antimicrobial preventive netting 300 deployed below the brim of a baseball cap 302 whereby the netting 300 can extend in front of the face and fully encompass the user's head. The antimicrobial preventive netting 300 can be attached to the brim of the cap 302 by any suitable means, such as hook and loop fasteners, buttons, snaps, and the like, or more permanent means, such as by sewing, heat welding, adhesives, and the like.

Figure 4:
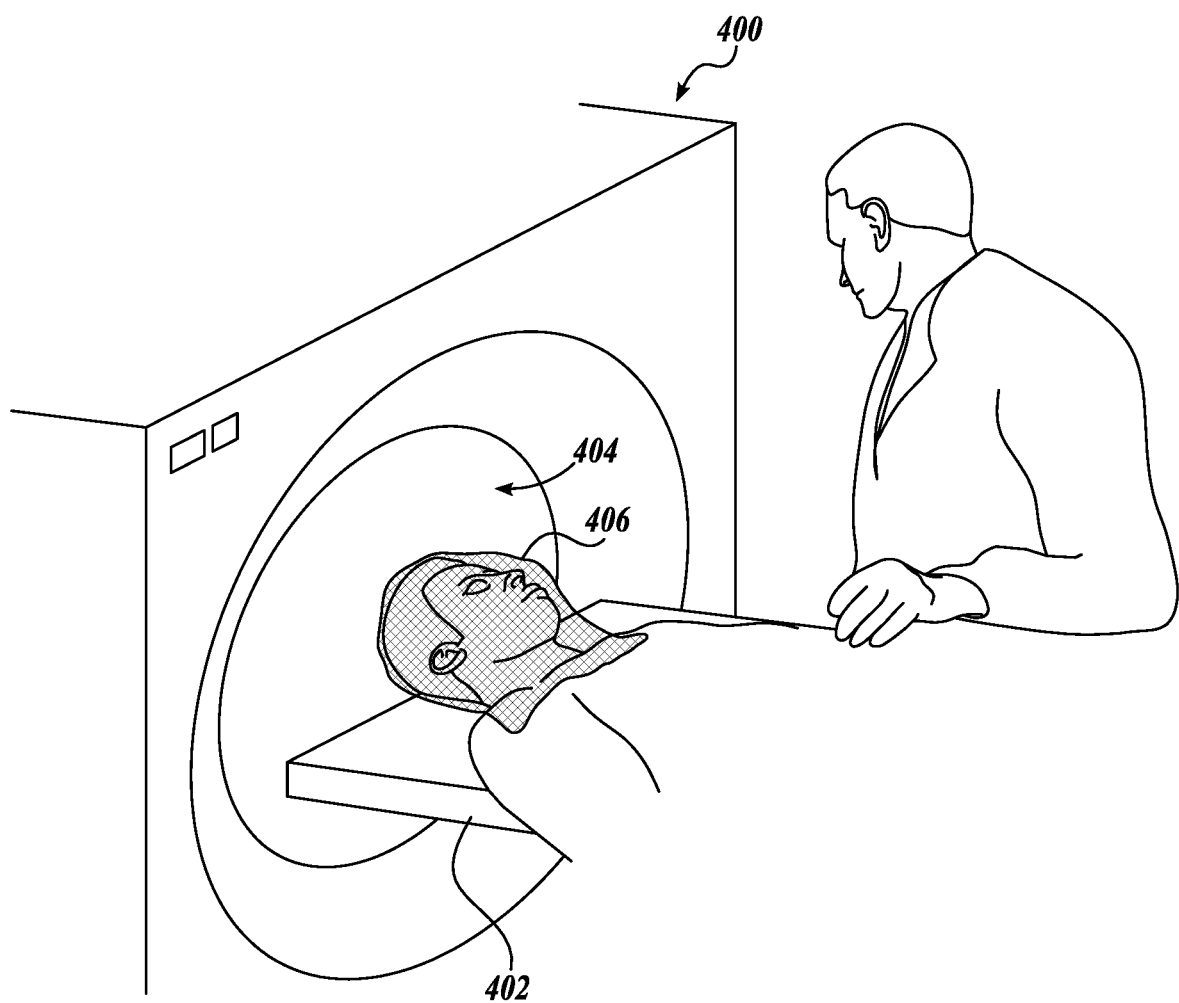
FIG. 4 is a diagrammatical illustration of using antimicrobial preventive netting on a user according to one embodiment.

FIG. 4 shows a magnetic resonance imaging scanner or computed tomography scanner 400 and sliding table 402 entering the bore 404. A patient resting on the table 402 is provided with antimicrobial preventive netting 406 encompassing the patient's head and face providing protection to doctors and staff operating the scanner 400. In this embodiment, the antimicrobial preventive netting may be configured as "bag" shape that can fit over the patient's head through an opening in the bag.

Figure 5:
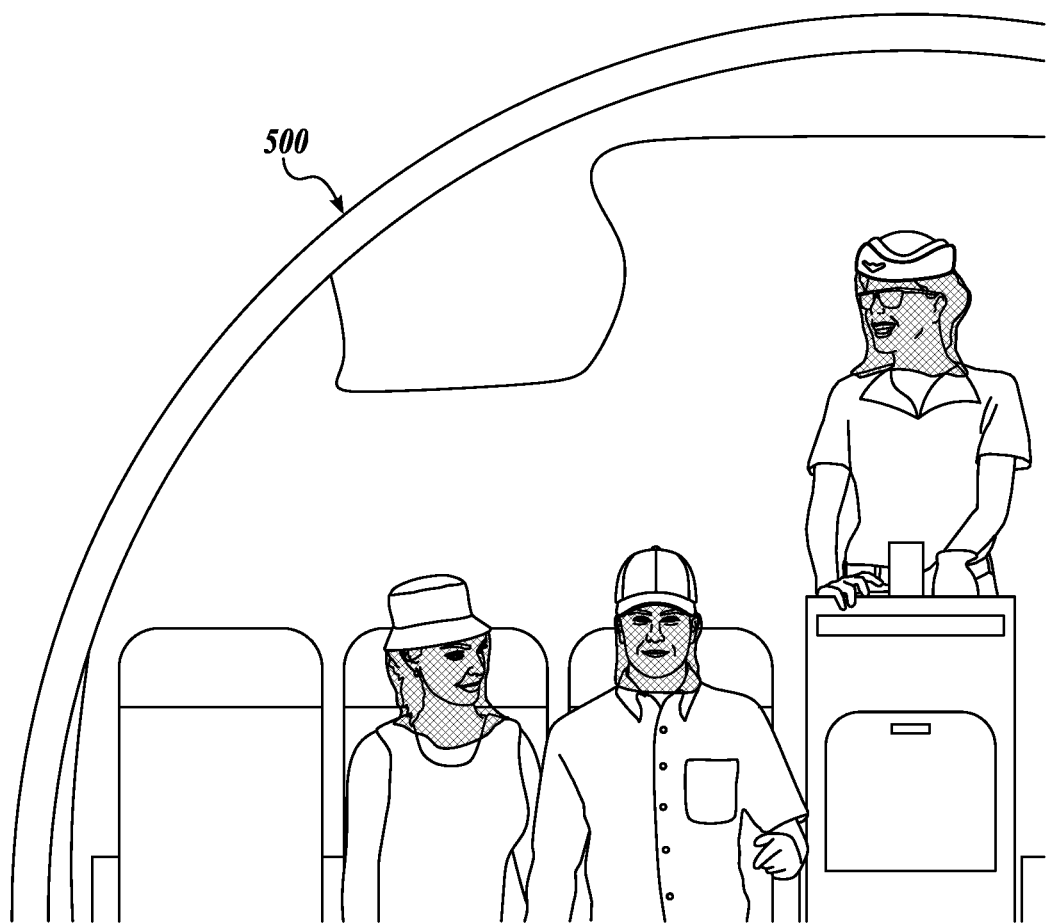
FIG. 5 is a diagrammatical illustration of using antimicrobial preventive netting on headgear for passengers and crew according to one embodiment.

FIG. 5 shows an aircraft fuselage 500 with passengers and crew wearing hats with antimicrobial preventive netting 502 encompassing the passenger's and crew's head and face for providing personal protection for all persons on the aircraft.

In some embodiments, a clear thin plastic segment is glued or otherwise attached to the netting in front of the eyes to improve the user's vision through the netting. Clear transparent plastic sheets or films can be incorporated for any netting uses where eye level sight lines are required.

In addition to use with headgear for head and face coverings, the antimicrobial preventive netting according to this disclosure may be constructed into enclosures and/or screens to surround larger spaces. Furthermore, instead of headgear that adds support to the antimicrobial preventive netting, the netting may be supported by rigid structural members forming a frame to which the netting may be attached.

Figure 6:
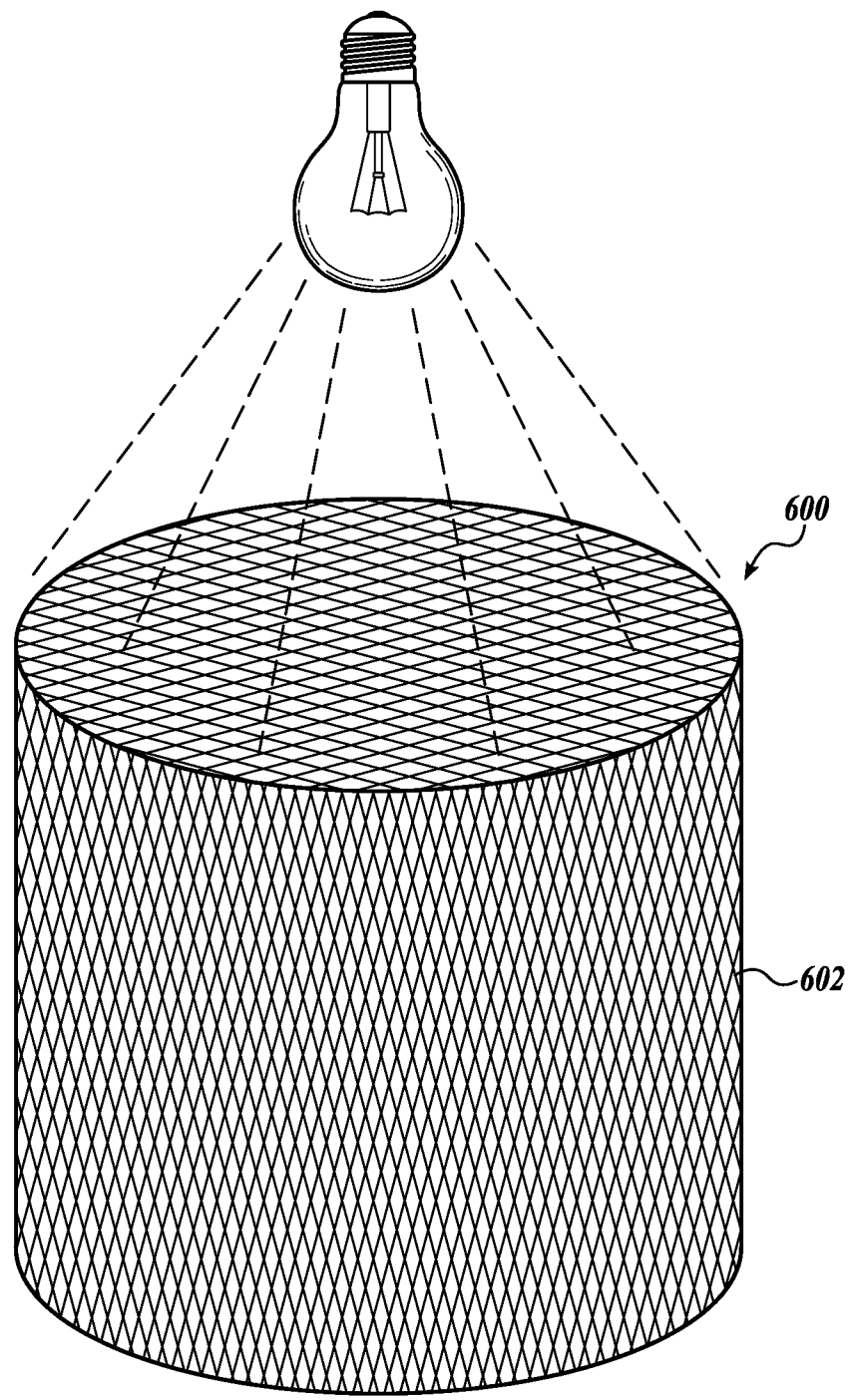
FIG. 6 is a diagrammatical illustration of an enclosure constructed of antimicrobial preventive netting according to one embodiment.

FIG. 6 is an illustration of one example of a rigid enclosure 600 made from antimicrobial preventive netting 602. The size and shape of any enclosure made from antimicrobial preventive netting will depend on the application. In some embodiments, an enclosure can be sized for wearing over and covering only the head. In some embodiments, an enclosure can be sized to protect an entire person, or a person at a workstation, such as in an office environment.

In some embodiments, an enclosure of antimicrobial preventive netting is made by incorporating a circular wire comprised of a metal, such as nitinol or other flexible metal, or comprised of a polymer which is flexible. The wire is configured to hold the netting away from the user, especially in windy conditions, or if the user is bending his/her head or torso in such a way that the netting may come in contact with the user. In another embodiment, the netting extends down to the feet of the user, completely surrounding the user.

Figures 7, 8:
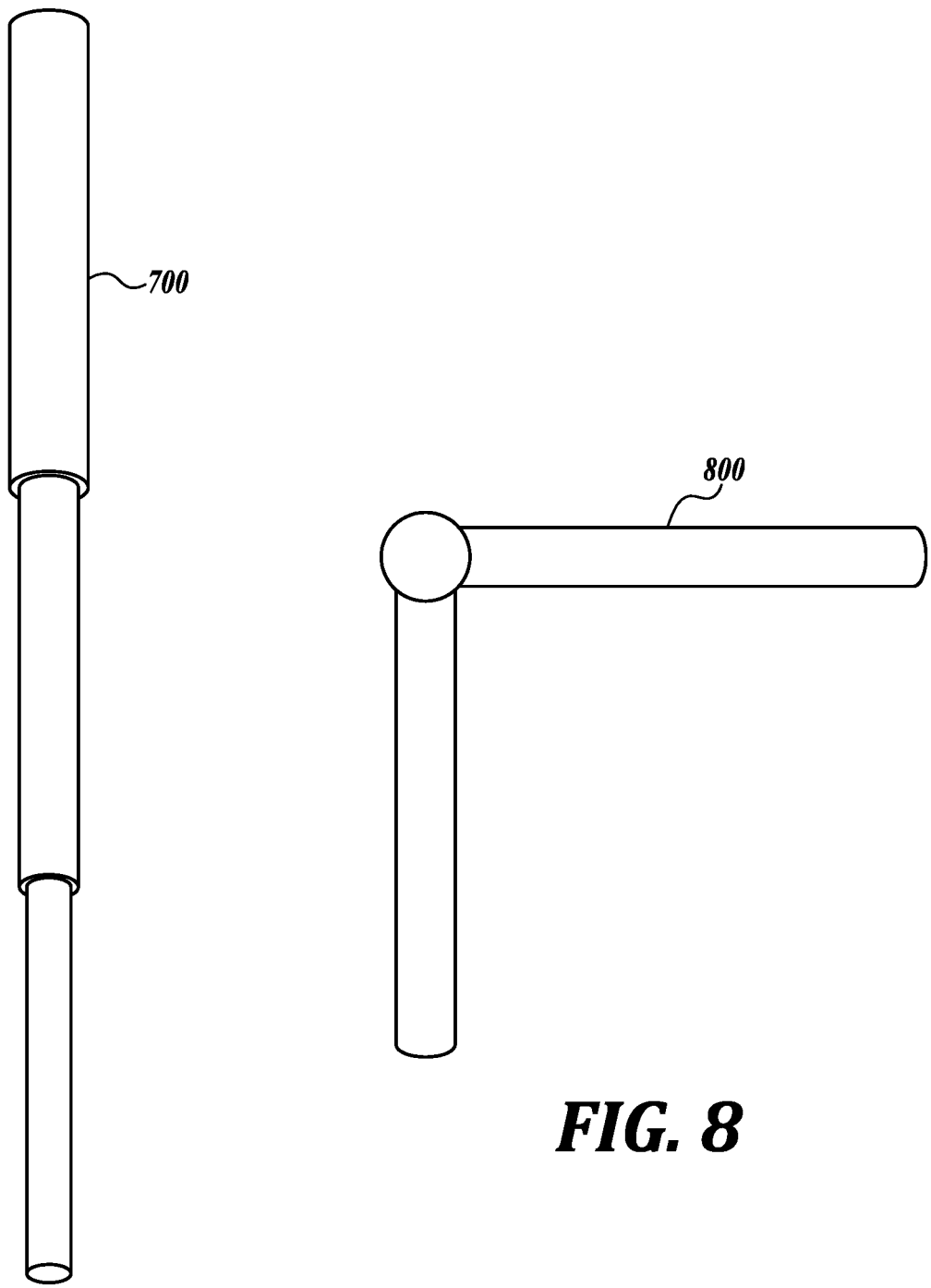
FIG. 7 is a diagrammatical illustration of a structural element for creating enclosures of antimicrobial preventive netting according to one embodiment.
FIG. 8 is a diagrammatical illustration of a structural element for creating enclosures of antimicrobial preventive netting according to one embodiment.

In some embodiments, any rigid netting enclosure may use a telescoping rod 700, such as illustrated in FIG. 7. In some embodiments, an antimicrobial preventive netting enclosure can be constructed by using a plurality of telescoping rods 700. The telescoping rods 700 may be flexible along the length to allow creation of curved enclosures. Generally, the telescoping rods 700 can flex to conform to the shape of the netting. A plurality of telescoping rods 700 may fit into pre-made pockets or loops fabricated into the antimicrobial preventive netting at the edges.

In some embodiments, a rigid netting enclosure may also use a hinged rod 800 as shown in FIG. 8. Hinged rod 800 can be bent at any angle or straight and then tightened to hold the angle. To disassemble, the hinged rod 800 can be untightened for folding into a compact length. Rods 700 and 800 are intended to be inserted along the edges of antimicrobial preventive netting to provide a frame that stretches out the antimicrobial preventive netting in the desired orientation.

Figure 9:
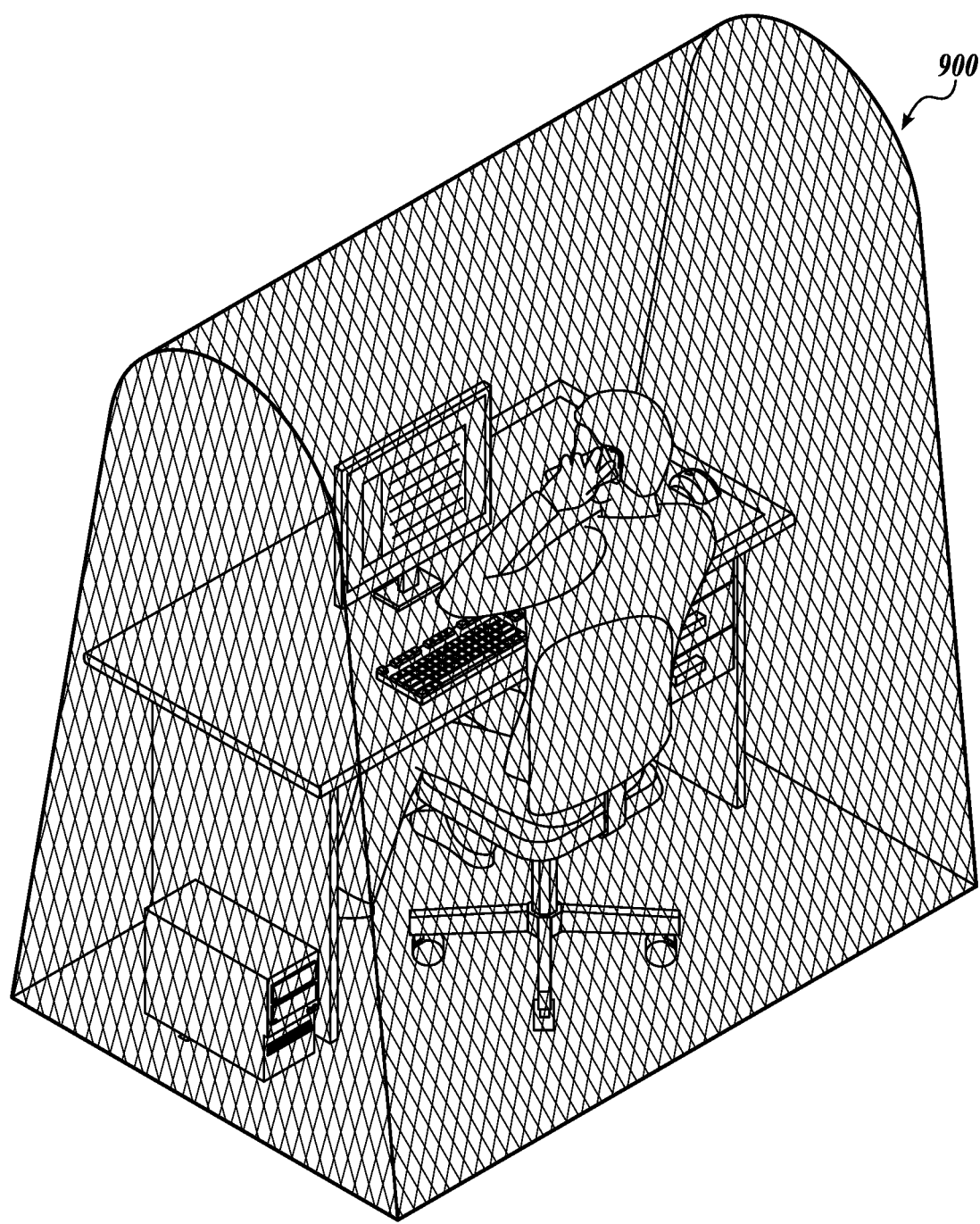
FIG. 9 is a diagrammatical illustration of an enclosure constructed of antimicrobial preventive netting according to one embodiment.

FIG. 9 is an illustration of a rigid antimicrobial preventive netting enclosure 900 that can encompass an entire workstation. A student, for example, is shown sitting at a desk surrounded by the protective antimicrobial preventive netting 900 which is configured as a half cylinder anteriorly and reaches down to the floor posteriorly. Classrooms or office environments can be provided with enclosures, such as enclosure 900, to protect students and employees from infecting one another.

In some embodiments, the netting is configured as a moveable, portable screen, which can be folded, rolled, or otherwise collapsed into a container, bag, or backpack and the like for ease of transport and deployment. The netting material can be designed and manufactured such that the edges of the material are slotted or folded into a small diameter cylinder in order to accommodate at least one stiffening telescoping rod 700 or hinged rod 800 which acts as a support member, and which can be reversibly connected to like members in order to create a vertical screen on at least one side of the user.

In some embodiments, multiple screens are joined to create a four-sided box with or without a screen roof around the user. The screen or screens are preferably oriented in a vertical fashion to provide protection to the user when sitting or standing upright. In some embodiments, the screen is oriented in a horizontal fashion around the user who is in a reclining or horizontal position. The stiffening rods can be rigid, broken down into sections for ease of storage and transport, or flexible in order to enable dome shapes to be created by the user.

In some embodiments, wheels are attached to the rods which enables ease of movement of the assembled enclosures of rods and netting, which protects the user from microbial infections. In some embodiments, the ends of the rods can incorporate removeable stands in contact with flooring such that the netting assembly can be free standing. In some embodiments, the rods incorporate at least one handle so that the user can move the netting as the user moves.

In some embodiments, the netting is sewn or glued such that it contains a rolled cylindrical edge that can accommodate rods which may be polymeric, plastic, metallic, or wood, which hold the netting in the desired configuration. The configuration can surround the user as a cylinder, a box, in a dome shape above the user's head, or as a tent with the apex above the user's head. In some embodiments, clamps are supplied with the netting material to enable ease of fastening the netting material to tables, desks, counters, chairs, seats, office cubicles, and to other fixtures and objects that enable shielding of individuals who are in relatively close proximity.

In some embodiments, the netting is manufactured to include a surface with multiple micro or macroscopic projections from both net surfaces, which greatly increases the surface area over which at least one photosensitizer can be applied, and which greatly increases the amount of singlet oxygen which can diffuse proximate to the netting surfaces, and on the netting surface itself.

EXAMPLES

Example 1

The specific polymeric material, the material thickness, hole size and shape, are optimized in the laboratory setting for 1) microbial droplet filtration, 2) Photosensitizer retention on netting material, 3) Maximal transparency, 4) Reduced movement of the netting material in windy conditions, 5) Minimal material degradation when washed multiple times.

Example 2

The photosensitizer composition, concentration, and volume is optimized in the laboratory setting for 1) Photosensitizer retention on netting, 2) Effective antimicrobial singlet oxygen generation, 3) Prolonged generation of antimicrobial singlet oxygen from the netting.

Example 3

A cloud of antimicrobial singlet oxygen is generated on both sides of the netting with a maximum depth of the singlet oxygen cloud less than 0.7 centimeters from the netting surface, which is a distance that precludes inadvertent injury to the user's face, hair, or head.

Example 4

The netting configuration enables effective use for individuals with facial hair and long hair, by holding the netting away from the user's surface by way of a polymeric or metallic flexible wire with spring-like properties. The netting configuration also prevents contact of the netting material with the user's face and body or clothing when the user is bending his/her head or torso.

Example 5

The top of the netting is supplied with an incorporated elastic band which enables a close comfortable fit that is secure over the surface of a hat or cap with a brim shading the face, or a sunhat type of design with a brim all the way around the user's head.

Example 6

The triboelectric effect is utilized to electrically charge the netting material, as the container which can be comprised of any metallic material capable of inducing the electric charging effect onto the netting material, is rotated.

Example 7

A rectangular optically clear thin plastic is incorporated into the netting in front of the face at eye level to improve the user's vision.

Example 8

Netting is supplied as square or rectangular sheets with edges that are rolled into a hollow cylinder, which accommodate thin, lightweight plastic or polymeric stiffening rods.

The ends of the rods incorporate a connection mechanism enabling the user to fashion a screen, with one or more sides and a roof if desired, which surrounds the user partially or completely. The rods can be manufactured so that they are telescoping, enabling the netting to be set up at different heights. The rods can also be supplied with a hinge mechanism which enables them to be stored and transported easily. The netting and support rods can also be manufactured so as to assume a shape surrounding the user, e.g., dome, cone, sphere, pyramid, cube, cuboid, tent, tube, or cylinder. A modular kit can be supplied to a user or group of users, incorporating various rod lengths, with fasteners, which enable various configurations of the netting for the best fit in various situations. Attachable and detachable wheels are provided that are fitted to the bottom of the netting and rod enclosure, which allow the enclosure to be moved with the user who is within the protective netting, for example, if waiting in a slow moving line or queue.

Example 9

The user wearing the netting hanging from a hat can easily eat by reaching underneath the netting with one hand. A straw can be inserted through a very small netting flap positioned in front of the user's mouth for safe imbibing of liquids.

Example 10

Nursing homes, care homes, and various long-term care facilities have been termed "ground zero" during the COVID-19 viral pandemic due to the disproportionate rate of deaths that occur in these settings. This disclosure enables the creation of antimicrobial protective netting around the bed of the patients, setting up a screen attached to a walking assist device surrounding the patient, or free standing, which can be moved with the patient by a caregiver helping the patient to ambulate. Wearing of masks by patients may not be feasible or tolerated, especially by mentally impaired and demented patients. Wearing the netting around the head may be far better tolerated. Patients can be fed by caregivers by reaching under the netting worn by the patient. Friends, family, relatives, significant others can wear the head netting, and/or netting surrounding the body to more safely visit these types of settings. The staff in these facilities can also benefit from the use of netting worn personally, and/or as a barrier to reduce infection risk to themselves and reduce contamination which may infect others. Optically transparent or translucent netting would be far less intrusive and frightening to patients with dementia as well. The use of netting in these settings is more practical and acceptable than requiring conventional personal protective equipment and gear which may not be available and requires special training for use.

Example 11

A formulation of methylene blue, riboflavin, and erythrosine is created using varying concentrations of each photosensitizer, starting at 0.00001 mg per liter solution and ranging up to the number of grams that almost saturates the solution (just prior to the concentration of photosensitizer that leads to precipitation) for each photosensitizer, and combining various doses such that one photosensitizer is combined at a higher or equal concentration to the other photosensitizers, testing various concentrations of photosensitizer combinations under different interior and outdoor lighting conditions. A matrix of different doses is created, with testing at various light fluence rates, in order to determine a useful range of singlet oxygen generation over a useful period of time that may last hours.

As an example of determining optimal photosensitizer concentrations and volumes, a calculation can be made using the known quantum yield in a waveband absorbed by the photosensitizer, incorporating the spectrum of the light source, for example typical indoor ambient lighting, or outdoor sunlight, and calculating singlet oxygen production at the difference fluence rates expected for different lighting conditions. Then, by testing photobleaching rates over time for photosensitizers at different concentrations and volumes, a useful range of concentrations and volumes can be derived for each photosensitizer and desired length of time interval till reapplication of the photosensitizer is required.

A proprietary photosensitizer formulation containing methylene blue, riboflavin, and erythrosine is tested for overall singlet oxygen generation in various ambient lighting conditions. Methylene blue is associated with a quantum yield of 0.52, riboflavin is associated with a quantum yield of 0.375 or higher depending on the test conditions, and erythrosine is associated with a quantum yield of around 0.6. White light created by LED combinations and constructs can incorporate varying ratios of red, green, and blue light, and exhibit variable spectral output distributions and characteristics. In general, there tends to be less red light output compared to red and yellow-green light. Since methylene blue absorbs in the red, and since there tends to be less available red light in white light LEDs, the methylene blue concentration and total amount can be less, compared to riboflavin which absorbs blue light, and erythrosine which absorbs in the green spectrum.

In some embodiments, an example of a formulation which takes into account the lower amount of available red light would be a ratio in grams of methylene blue to erythrosine to riboflavin of 1:2:2 respectively. In this manner, the total amount of photosensitizers in combination is minimized while enabling adequate singlet oxygen output.

Therefore, antimicrobial preventive netting and a light source, comprising more than one photosensitizers, can be provided wherein a ratio of the more than one photosensitizers is based on a quantum yield of each of the more than one photosensitizers that is produced when absorbing a waveband of light generated by the light source.

Therefore, antimicrobial preventive netting and a light source, comprising more than one photosensitizers, can be provided wherein the light source is configured to emit wavebands of light that result in a highest quantum yield for each of the more than one photosensitizers Example 12

Radiology departments are a central hub for medical care given almost all patients who seek care through the emergency department or admitted to the hospital undergo radiological examinations for determination of diagnosis which then dictates treatment. Therefore, radiology technologists, computed tomography scanners, magnetitic resonance scanners, and ultrasound examination rooms are extremely susceptible to contamination by a known infectious patient or a patient of unknown infectivity. During the current COVID-19 pandemic, it is common practice to vacate the CT or MRI scanner for one or more hours for thorough decontamination to be performed. This COVID-19 decontamination process is extremely problematic for a hospital's workflow given that in a busy ER, a single CT scanner can and needs to be scanning four or more patients per hour. Further, this process delays diagnosis for patients and has the potential to hinder patient care. Another problem arises when trauma patients are brought to the scanner and require immediate scanning to diagnose life threatening injuries. There is no time to test individuals for COVID-19 prior to scanning and some injuries and interventions inherently cause aerosolization of microbial droplets putting the treatment team at risk and also contaminating equipment. Therefore, the use of the antimicrobial preventive netting used on the patient and treatment team would reduce the risk for equipment and personnel contamination and in addition limit infection risk to unsuspecting subsequent patients who enter the radiology exam room.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While illustrative embodiments have been illustrated and described, it will be appreciated that various changes can be made therein without departing from the spirit and scope of the invention.

The embodiments of the invention in which an exclusive property or privilege is claimed are defined as follows:

1. A antimicrobial preventive netting, comprising:
   the netting having a plurality of openings between a top surface and a bottom surface; and
   photosensitizers that are distributed on the top surface, the bottom surface and through the plurality of openings, wherein the photosensitizers generate a cloud of singlet oxygen on the netting in response to incident light, wherein the photosensitizers include methylene blue, erythrosine, and riboflavin, wherein the amount of methylene blue is less than an amount of erythrosine or an amount of riboflavin, wherein a ratio of methylene blue to erythrosine to riboflavin is 1:2:2.

2. The antimicrobial preventive netting of claim 1, wherein the cloud of singlet oxygen on the netting, further comprises a maximum depth of less than 0.7 centimeters from the top surface and bottom surface of the netting.

3. The antimicrobial preventive netting of claim 1, wherein an amount of the photosensitizers is in a range from 0.05 µM to 1000 µM, wherein the photosensitizers are contained within the netting or on exterior surfaces of the netting, and wherein the amount of the photosensitizers generates the cloud of singlet oxygen in response to 100 lux or more of the incident light photoactivating the photosensitizers for 60 minutes or more.

4. The antimicrobial preventive netting of claim 1, wherein the photosensitizers, further comprise electrically charging one or more photosensitizers to attract and retain opposite electrically charged microbial particles and/or microbial droplets for inactivation.

5. The antimicrobial preventive netting of claim 1, wherein the plurality of openings through the antimicrobial preventive netting traverse across a thickness of the netting between the top surface and the bottom surface.

6. The antimicrobial preventive netting of claim 5, further comprising one or more of fibers or threads running in two or more distinct directions such that the one or more fibers or threads placed in a first direction are spaced apart, and the one or more fibers or threads placed in a second direction are spaced apart to define an arrangement of the plurality of openings through the antimicrobial preventive netting.

7. The antimicrobial preventive netting of claim 1, further comprises one or more electret materials including one or more of synthetic polymers, fluoropolymers, polypropylene, or polyethyleneterephthalate.

8. The antimicrobial preventive netting of claim 1, further comprises one or more of a metallic material, a conductive material, a composite material, a ceramic material, or a three dimensional printed material.

9. The antimicrobial preventive netting of claim 1, further comprising: a light source; and
   wherein a ratio of two or more photosensitizers is based on a quantum yield of each of the two or more photosensitizers in response to a waveband of incident light emitted by the light source.

10. The antimicrobial preventive netting of claim 1, further comprising:
    a frame that forms one or more of an enclosure or a screen, wherein the frame is capable of supporting the antimicrobial preventive netting as it covers one or more surfaces of the enclosure or the screen.

11. The antimicrobial preventive netting of claim 10, wherein the frame further comprises:
   one or more telescoping rods, hinged rods, or flexible metal wire.

12. The antimicrobial preventive netting of claim 1, further comprising:
   headgear for a user, wherein the antimicrobial preventive netting is connected to one or more portions of the headgear and is capable of covering a face of the user.

13. A method of making antimicrobial preventive netting, comprising:
   placing the netting within a container having a body defining a cavity;
   adding a solution of photosensitizers inside the cavity of the container; and
   rotating the container to enable the solution of the photosensitizers to be deposited on each surface of the netting, and wherein a plurality of openings are defined through the netting to produce an antimicrobial preventive netting, comprising:
   the plurality of openings are between a top surface and a bottom surface of the netting; and
   photosensitizers that are distributed on the top surface, the bottom surface and through the plurality of openings, wherein the photosensitizers generate a cloud of singlet oxygen on the netting in response to incident light, wherein the photosensitizers include methylene blue, erythrosine, and riboflavin, wherein the amount of methylene blue is less than an amount of erythrosine or an amount of riboflavin, wherein a ratio of methylene blue to erythrosine to riboflavin is 1:2:2.

14. The method of claim 13, wherein the container is made from a metal, and the method further comprising electrically charges the netting by rotating the netting within the metal container.

15. The method of claim 14, further comprising reapplying one or more photosensitizers to the antimicrobial preventive netting.

* * * * *

UNITED STATES PATENT AND TRADEMARK OFFICE
CERTIFICATE OF CORRECTION

PATENT NO. : 11,425,905 B2
APPLICATION NO. : 17/244688
DATED : August 30, 2022
INVENTOR(S) : J. Chen et al.

It is certified that error appears in the above-identified patent and that said Letters Patent is hereby corrected as shown below:

In the Claims

| Column | Line | |
|---|---|---|
| 16 | 15 | Claim 14 change "charges" to -- charging --. |

Signed and Sealed this
Fifth Day of September, 2023

Katherine Kelly Vidal
*Director of the United States Patent and Trademark Office*